US006921819B2

(12) United States Patent
Piron et al.

(10) Patent No.: US 6,921,819 B2
(45) Date of Patent: Jul. 26, 2005

(54) POLYSACCHARIDE CROSSLINKING, HYDROGEL PREPARATION, RESULTING POLYSACCHARIDE(S) AND HYDROGEL(S), USES THEREOF

(75) Inventors: Estelle Piron, Villeneuve-Tolosane (FR); Raymonde Tholin, Annecy (FR)

(73) Assignee: Laboratoires d'Esthetique Appliquee, Paris (FR)

( * ) Notice: Subject to any disclaimer, the term of this patent is extended or adjusted under 35 U.S.C. 154(b) by 0 days.

(21) Appl. No.: 10/332,727

(22) PCT Filed: Jul. 16, 2001

(86) PCT No.: PCT/FR01/02300

§ 371 (c)(1),
(2), (4) Date: Jan. 13, 2003

(87) PCT Pub. No.: WO02/06350

PCT Pub. Date: Jan. 24, 2002

(65) Prior Publication Data

US 2003/0148995 A1 Aug. 7, 2003

(30) Foreign Application Priority Data

Jul. 19, 2000 (FR) .......................................... 00 09497

(51) Int. Cl.[7] ........................... C07H 5/04; C07H 5/06; C07H 1/00; C07H 1/06

(52) U.S. Cl. ..................... 536/55.3; 536/55.1; 536/106; 536/124; 536/127

(58) Field of Search ............................ 536/55.3, 55.1, 536/106, 124, 127

(56) References Cited

U.S. PATENT DOCUMENTS 5,783,691 A * 7/1998 Malson et al. ............. 536/55.1
6,358,580 B1 * 3/2002 Mang et al. ................ 428/35.7
6,368,356 B1 * 4/2002 Zhong et al. ............. 623/23.75

FOREIGN PATENT DOCUMENTS

CA 949965 A * 6/1974

* cited by examiner

Primary Examiner—James O. Wilson
Assistant Examiner—Everett White
(74) Attorney, Agent, or Firm—Klauber & Jackson

(57) ABSTRACT

The invention relates to a process for the crosslinking of polysaccharides. The process of the invention is a process for the crosslinking of at least one polymer selected from polysaccharides and their derivatives, under the action of at least one polyfunctional crosslinking agent, characterized in that said polyfunctional crosslinking agent is reacted with said polymer, in the solid state, during hydration. The invention is applied to the manufacture of hydrogels and gels that can be used, in particular, in plastic or cosmetic surgery.

8 Claims, 2 Drawing Sheets

Figure 1:
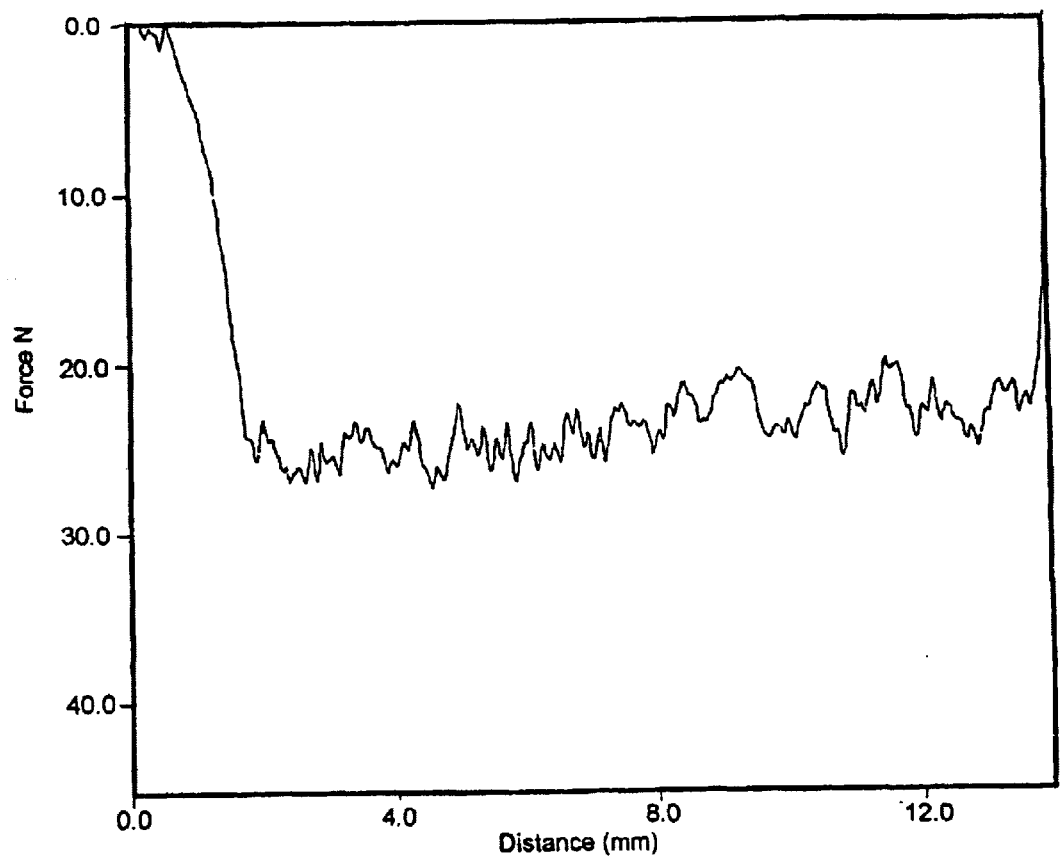

POLYSACCHARIDE CROSSLINKING, HYDROGEL PREPARATION, RESULTING POLYSACCHARIDE(S) AND HYDROGEL(S), USES THEREOF

The present invention relates to:

a novel process for the crosslinking of at least one polymer selected from polysaccharides and their derivatives;

a process for the preparation of an injectable hydrogel of at least one such polymer;

the crosslinked polymers and injectable hydrogels obtainable respectively by each of said processes; and a filling material, useful in plastic surgery or cosmetic surgery, based on such hydrogels.

Hydrogels, especially injectable hydrogels, have been prepared from polysaccharides and their derivatives—particularly from hyaluronic acid, its salts and their mixtures—which have a zero, low or high degree of crosslinking. Patent application EP-A-0 161 887 thus describes the use of such injectable hydrogels for the treatment of arthritis. Patent applications WO-A-96/33751 and WO-A-00/01428 describe injectable biphase compositions whose continuous phase is based on such a hydrogel. Said continuous phase serves as an injection vehicle.

According to the teaching of these documents (according to the teaching of the prior art, to the knowledge of the Applicant), the crosslinking of the polymer, particularly that of sodium hyaluronate fibers, is effected in the presence of a crosslinking agent, especially a polyepoxide, a controlled amount of said crosslinking agent reacting with said polymer dissolved in a basic medium. The reaction in question is a gel/liquid reaction. Its purpose is to generate a crosslinked product of maximum possible homogeneity as the precursor of a viscoelastic gel that is readily injectable and as far as possible devoid of "flakes", or local overcrosslinking.

The presence of these "flakes" is highly detrimental to the injectability of the gel in question. When it is injected, greater forces have to be applied when such a "flake" becomes blocked in the injection needle. This problem is all the more critical because the injection needles used may have very small diameters.

It is with reference to this technical problem of optimizing the injectability of hydrogels based on such crosslinked polymers that the present invention was developed.

Said present invention in fact proposes a novel method of carrying out the crosslinking such that the crosslinked polymer produces, after hydration, a very homogeneous hydrogel (virtually) devoid of local overcrosslinking, which can be injected with high precision.

CA-A-949 965 has described another novel method of crosslinking to give starch granules, according to which the operation comprises three main steps:

a first step for hydrating starch granules, during which said granules become charged with sodium hydroxide solution and crosslinking agent (epichlorohydrin);

a second step for recovering the charged granules, particularly by filtration or centrifugation; and a third step for crosslinking said recovered charged granules by heating.

Said crosslinking is carried out on granules after they have been hydrated. The granules obtained are homogeneous in their bulk, but together they do not constitute a large volume perfectly homogeneous in its bulk.

According to the invention, to obtain a polymer crosslinked very homogeneously in its bulk, the crosslinking is carried out at the same time as the hydration, more precisely as said hydration is taking place. According to the invention, it is thus possible to obtain large volumes perfectly homogeneous in their bulk (isotropically crosslinked).

The first subject of the present invention is therefore a process for the crosslinking of at least one polymer selected from polysaccharides and their derivatives. Conventionally, the crosslinking in question is carried out in the presence of at least one polyfunctional (at least bifunctional) crosslinking agent.

According to the invention, the process is characterized in that said polyfunctional crosslinking agent is reacted directly with said polymer, in the solid state, during hydration.

Therefore, within the framework of the process of the invention, said polymer is not preconditioned, in the sense of the prior art, by dissolution/swelling.

Totally surprisingly, under the conditions of the invention the crosslinking is a solid/liquid reaction which generates a homogeneously crosslinked polymer, said polymer being the precursor of a hydrogel of perfectly homogeneous structure.

Preferably, said polyfunctional crosslinking agent is reacted with said solid polymer in basic solution. Thus said polyfunctional crosslinking agent can be either dissolved or suspended in a basic solution, this solution or suspension then being reacted directly with said polymer in the solid state, or reacted directly with said polymer in the solid state, the basic agent being added simultaneously with the crosslinking agent, but by a separate means of introduction, to said polymer in the solid state.

Generally, when said crosslinking agent is in basic solution, this basic solution has a pH of between 10 and 12.

As crosslinking agent it is possible to use any agent known for crosslinking polysaccharides and their derivatives via their hydroxyl groups, said crosslinking agent being at least bifunctional and especially an epoxide or its derivatives.

Such crosslinking agents which can be used in particular are 1,4-butanediol diglycidyl ether (or 1,4-bis(2,3-epoxypropoxy)butane or 1,4-bisglycidyloxybutane= BDDE), 1,2-bis(2,3-epoxypropoxy)ethylene and 1-(2,3-epoxypropyl)-2,3-epoxycyclohexane.

The use of several crosslinking agents is not excluded from the framework of the invention.

It is very particularly recommended to use 1,4-butanediol diglycidyl ether (BDDE).

Said polymer(s) in question is (are) selected from polysaccharides, their derivatives and their mixtures. It is (they are) selected especially from hyaluronic acid and its salts, chondroitin sulfates, keratan sulfates, heparin, alginic acid, starch, carbomethyl cellulose, hydroxypropyl methyl cellulose, chitosan and their mixtures.

Hyaluronic acid, its salts and their mixtures are particularly preferred.

Sodium hyaluronate is very particularly recommended.

The crosslinking to be carried out on said polymer is within the scope of those skilled in the art. For each polymer those skilled in the art will know how to optimize the conditions of this crosslinking according to the nature of said polymer, and how to carry out said crosslinking to an optimized degree.

In fact, the degree of crosslinking must be sufficient for the hydrogel obtained from this crosslinked polymer to remain implanted at the injection site without excessive diffusion away from this injection site, but it must remain reasonable for use, particularly by injection.

According to the invention, however, the polymer is preferably crosslinked, via its hydroxyl groups, by means of said crosslinking agent to a degree of crosslinking defined by a ratio $$R = \frac{\text{Total number of reactive groups in said crosslinking agent}}{\text{Total number of disaccharide units in the hyaluronic acid molecules}}$$

of between 0.10 and 0.50.

The second subject of the invention is the crosslinked polymer obtainable by carrying out the crosslinking process of the invention as described above in each of its variants.

The third subject of the invention is a process for the preparation of an injectable hydrogel of at least one crosslinked polymer selected from polysaccharides and their derivatives.

Characteristically, this process comprises the crosslinking of said polymer by the crosslinking process of the invention described above in all its variants, said crosslinking being followed by the swelling of said crosslinked polymer by hydration.

The process for the preparation of an injectable hydrogel of the invention is optimized in terms of the presence of crosslinking or local overcrosslinking within said hydrogel.

Said process for the preparation of said hydrogel is furthermore optimized per se in terms of the time taken to carry it out.

According to the invention a crosslinked hydrogel can thus be obtained in 2 to 3 hours by means of a solid/liquid phase reaction, whereas according to the prior art a crosslinked hydrogel is obtained in about 5 h by means of a gel/liquid phase reaction.

This time saving is appreciable per se. It actually affords a better quality of final product by limiting the degradation of the polymer which takes place particularly in a basic medium. It also guarantees a better reproducibility of the synthesis of the gels ultimately obtained.

Characteristically, said process comprises the following successive steps:

the crosslinking of a polymer or mixture of polymers, selected from polysaccharides and their derivatives, by the crosslinking process described above, the swelling of said crosslinked polymer(s), the purification of said swollen crosslinked polymer(s), and the sterilization, if necessary, of said purified swollen crosslinked polymer(s).

The crosslinking, purification and sterilization steps are known per se to those skilled in the art. Said purification is necessary to remove the unreacted or incompletely reacted products such as the polymer(s) and the crosslinking agent (s). Said sterilization step is obviously necessary if the upstream steps have not been carried out under sterile conditions.

The fourth subject of the invention is the injectable hydrogel obtainable by carrying out said process for the preparation of an injectable hydrogel according to the third subject of the invention as described above in its different variants. This hydrogel is characterized by the presence of little or no local overcrosslinking.

The injectable hydrogel as described above, and as obtained by the above process, is perfectly suitable for the manufacture of a filling gel useful in plastic or cosmetic surgery.

The fifth subject of the invention is therefore a filling gel, useful in plastic or cosmetic surgery, which is based on a hydrogel according to the fourth subject of the invention and/or as obtained by the process according to the third subject of the invention.

The hydrogel of the invention constitutes at least the continuous phase of said filling gel of the invention.

Thus said filling gel can consist of a single phase which is the crosslinked hydrogel of the invention.

It can also be biphase or multiphase, i.e. it can consist of several phases of which at least the continuous phase is the crosslinked hydrogel of the invention.

The second and other phases can be beads, for example, which themselves consist of the crosslinked hydrogel of the invention, except that in this case the hydrogel constituting the beads has a higher degree of crosslinking than the crosslinked hydrogel constituting the continuous phase of the filling gel of the invention. The beads can also be made of acrylic or acrylic polymer.

Preferably, the filling gel according to the invention consists of a crosslinked hydrogel according to the invention. It is monophase.

The more or less crosslinked hydrogel(s) forming the base of the filling gel of the invention may or may not be charged. For example, they can be charged with antiseptics and optionally other substances whose presence is advantageous in the zones of the human or animal body in question.

Thus said hydrogel constituting at least the continuous phase of a filling gel of the invention advantageously contains deoxyribonucleic acid (DNA). This product is known to reduce the inflammatory reaction and promote tissue regeneration.

The filling gel of the invention has the advantage of being readily injectable, i.e. injectable through very fine needles of 26G to 30G without the need for pressure peaks; this is because the degree of crosslinking is homogeneous throughout the bulk of the crosslinked hydrogel used, which is obtained by the process of the invention.

This crosslinking homogeneity, coupled with the degree of crosslinking, results from the total or virtual absence of more highly crosslinked "flakes" in the gel, so this gel can be injected into the desired site with a constant force and hence with better precision.

The filling gel of the invention can be used in cosmetic surgery, for example for filling wrinkles in a more precise, more reliable and easier manner because, in contrast to the filling gels of the prior art, it has a very uniform injectability level.

Other objects, characteristics and advantages of the invention are now illustrated by means of the Examples below, which describe, with reference to FIGS. 1 and 2 attached, the preparation of a preferred filling gel according to the invention, the preparation of a filling gel of the prior art and the injectability tests performed on these gels.

Figure 2:
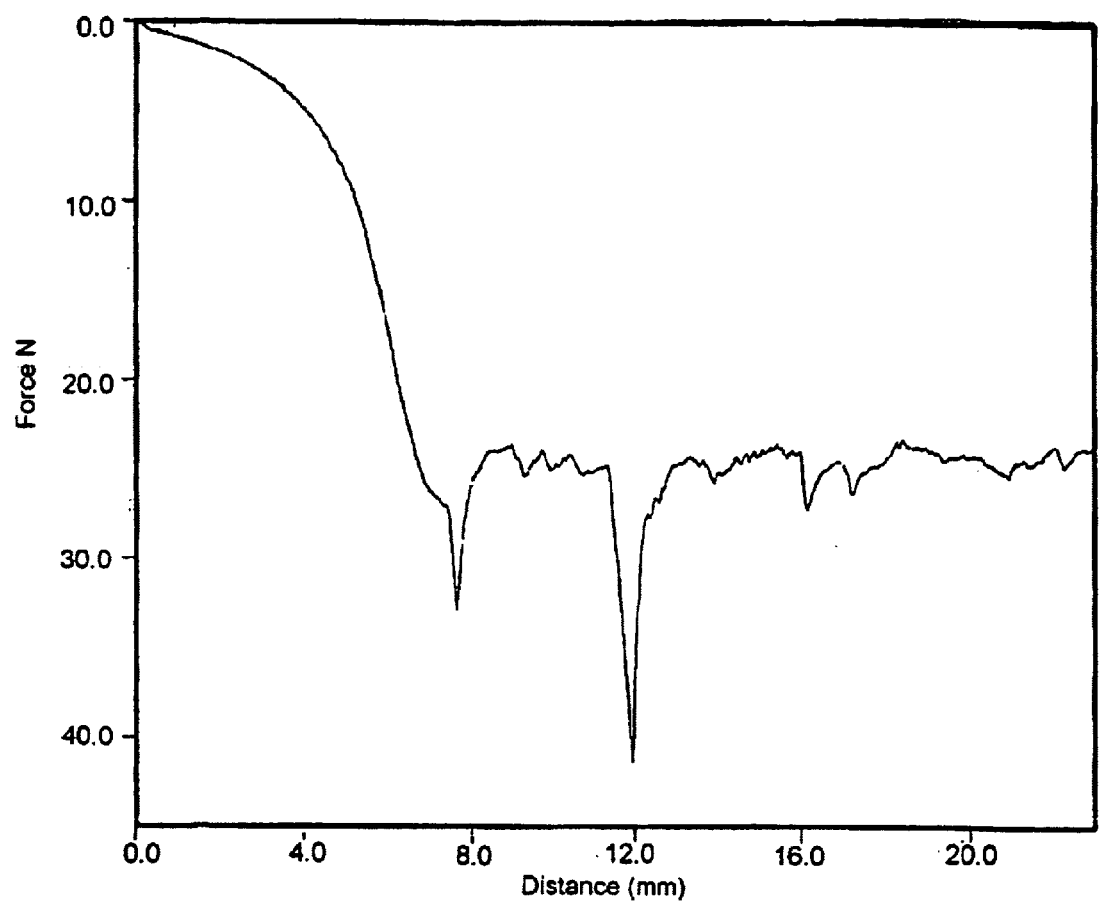

In the Figures:

FIG. 1 shows the injectability curve of the filling gel according to the invention prepared in Example 1, i.e. the force required to inject this gel as a function of the injection time; and FIG. 2 shows the injectability curve of the filling gel according to the prior art prepared in Example 2, i.e. the force required to inject this gel as a function of the injection time.

EXAMPLE 1

Preparation of a Filling Gel According to the Invention 1 g of predried fibers of sodium hyaluronate (NaHa, of molecular weight $M_w \approx 2.10^6$ Da) is weighed out into a first receptacle.

In a separate receptacle the chosen crosslinking agent, 1,4-butanediol diglycidyl ether (BDDE), is diluted in 1% sodium hydroxide solution to give a basic BDDE solution diluted to 1/100.

6.8 g of the previously prepared BDDE solution diluted to 1/100 are then added to the NaHa fibers, still in the solid state, and the mixture is homogenized mechanically with a spatula.

The mixture is then placed in a water bath at 50° C.±2° C. for 2 to 3 hours, with further homogenization after 15 minutes of immersion, to cause the NaHa polymer to crosslink.

The resulting crosslinked NaHa polymer is then immersed in a phosphate buffer (PB) to stabilize the pH. This step corresponds to the step in which the crosslinked NaHa polymer is swollen by hydration to give the hydrogel of the invention.

The swollen crosslinked NaHa polymer is then purified by immersion in different baths of phosphate buffer to remove unreacted crosslinking agent and NaHa.

The hydrogel obtained is then homogenized mechanically to ensure the final homogeneity, and packed into syringes which are sterilized in an autoclave.

As can be seen in this Example, the filling gel of the invention consists solely of the hydrogel obtained or obtainable by the process of the invention.

The gel obtained is injectable with a 27G1/2 or 30G1/2 cannula to increase volumes under the skin.

EXAMPLE 2

Preparation of a Filling Gel by the Process of the Prior Art 1 g of predried fibers of sodium hyaluronate (NaHa, of molecular weight $M_w \approx 2.10^6$ Da) is weighed out into a receptacle.

6.7 g of 1% sodium hydroxide solution are added to the same receptacle containing the NaHa fibers and the mixture is left to stand at room temperature for 2 h 30 min to 3 h 00 min with homogenization every ½ hour.

This step corresponds to the step in which the NaHa fibers are hydrated. The uncrosslinked NaHa polymer is obtained in the form of a gel.

60 mg of the same crosslinking agent as that used in Example 1, namely BDDE, are then added to the same receptacle containing the NaHa gel and the sodium hydroxide solution, and the BDDE is homogenized mechanically in the NaHa gel.

The mixture is then placed in a water bath at 50° C.±2° C. for 1 h 45 min to 2 h 30 min.

This step corresponds to the step in which the NaHa polymer is crosslinked.

The resulting crosslinked NaHa polymer is then immersed in a phosphate buffer (PB) to stabilize the pH. This step corresponds to the step in which the crosslinked polymer is swollen by hydration.

The swollen crosslinked NaHa polymer is then purified by immersion in different baths of phosphate buffer to remove any unreacted crosslinking agent and NaHa.

The hydrogel obtained is then homogenized mechanically to ensure the final homogeneity . . . packed into syringes which are sterilized in an autoclave.

In this Example the filling gel again consists solely of the purified and stabilized, swollen crosslinked hydrogel obtained by the process of the prior art.

EXAMPLE 3

Injectability Tests on the Filling Gels Obtained

To compare the injectability of the filling gel obtained by the process of the invention with that of the filling gel obtained by the process of the prior art, injectability tests were performed on each of them.

These injectability tests were performed on a VersaTest tension/compression tester (marketed by Mecmesin). The gels were each injected through a 27G1/2 needle at a compression rate of 12.5 mm/min. The force required to inject the gels, expressed in Newtons, is characteristic of the degree of crosslinking and the NaHa concentration of the gel, and the uniformity of this force is characteristic of the ease of injection of the gel and its homogeneity.

In fact, if the gel comprises more highly crosslinked flakes, the force required to inject the gel increases, and then decreases when the flake has passed through the needle; this manifests itself as peaks in the force required to maintain the injection rate of 12.5 mm/min.

The results of the measurements made on the filling gel of the invention are shown in the graph of FIG. 1 and the results of the measurements made on the filling gel manufactured by the process of the prior art are shown in the graph of FIG. 2.

In these graphs the force in Newtons (N) required to inject the gel is shown on the ordinate and the injection time, represented by the chart run in mm, is shown on the abscissa. It is pointed out that, in these Figures, an increase in the force required to inject the filling gel manifests itself as a falling peak relative to the base line.

As can be seen in FIGS. 1 and 2, the force required to inject the filling gel according to the invention is much more uniform: the mean force required is about 27 Newtons without the presence of peaks due to the presence of flakes. By contrast, although the mean force for injecting the filling gel manufactured by the process of the prior art is also about 27 Newtons, 2 significant peaks with amplitudes of 30 to 42 Newtons appear when the gel according to the prior art is injected. These peaks are characteristic of local over-crosslinking.

Thus the crosslinking of the gel obtained by the process of the invention is more homogeneous than that of the gel manufactured by the process of the prior art.

What is claimed is:

1. A process for the crosslinking of at least one polymer selected from hyaluronic acid, its salts and their mixtures, under the action of at least one polyfunctional crosslinking agent, characterized in that said polyfunctional crosslinking agent is reacted with said polymer, in the solid state, during hydration.

2. The crosslinking process according to claim 1, characterized in that said polyfunctional crosslinking agent reacts with said polymer in basic solution.

3. The cross linking process according to claim 1, characterized in that said polyfunctional crosslinking agent is an epoxide advantageously selected from 1,4 butanediol diglycidyl ether, 1,2-bis(2,3-epoxypropoxy)ethylene and 1-(2,3-epoxypropyl)-2,3-epoxycyclohexane.

4. The crosslinking process according to claim 3, characterized in that said polyfunctional crosslinking agent consists of 1,4-butanediol diglycidyl ether.

5. The crosslinking process according to claim 1, characterized in that said polymer is crosslinked, via its hydroxyl groups, by means of a crosslinking agent to a degree of crosslinking defined by a ratio $$R = \frac{\text{Total number of reactive groups in said crosslinking agent}}{\text{Total number of disaccharide units in the hyaluronic acid molecules}}$$

of between 0.10 and 0.50.

6. A process for the preparation of an injectable hydrogel of at least one crosslinked polymer selected from hyaluronic acid, its salts and their mixtures, characterized in that it comprises the crosslinking of said polymer according to claim 1, followed by the swelling of said crosslinked polymer by hydration.

7. A process for the preparation of an injectable hydrogel of at least one crosslinked polymer selected from hyaluronic acid, its salts and their mixtures, characterized in that it comprises:
 a) the crosslinking of said polymer according to claim 1;
 b) the swelling of said cross linked polymer;
 c) the purification of said swollen crosslinked polymer; and
 d) the sterilization, if necessary, of said purified swollen crosslinked polymer.

8. The process of claim 1 wherein the said polymer is sodium hyaluronate.

* * * * *